United States Patent
Gonzalez

(10) Patent No.: US 6,695,791 B2
(45) Date of Patent: Feb. 24, 2004

(54) SYSTEM AND METHOD FOR CAPTURING BODY TISSUE SAMPLES

(75) Inventor: Hugo X. Gonzalez, Woodinville, WA (US)

(73) Assignee: Spiration, Inc., Redmond, WA (US)

(*) Notice: Subject to any disclaimer, the term of this patent is extended or adjusted under 35 U.S.C. 154(b) by 5 days.

(21) Appl. No.: 10/039,104

(22) Filed: Jan. 4, 2002

(65) Prior Publication Data

US 2003/0130593 A1 Jul. 10, 2003

(51) Int. Cl.$^7$ ................................................ A11B 10/00
(52) U.S. Cl. ........................ 600/562; 600/565; 600/571; 606/110; 606/114; 606/115
(58) Field of Search .................... 600/562, 565, 600/569, 570, 571, 572; 606/110, 113, 114, 115

(56) References Cited

U.S. PATENT DOCUMENTS

| | | | |
|---|---|---|---|
| 3,889,657 A | * 6/1975 | Baumgarten | 600/571 |
| 4,870,975 A | * 10/1989 | Cronk et al. | 600/565 |
| 5,186,711 A | 2/1993 | Epstein | |
| 5,350,388 A | 9/1994 | Epstein | |
| 5,423,830 A | * 6/1995 | Schneebaum et al. | 606/115 |
| 5,575,293 A | * 11/1996 | Miller et al. | 600/562 |
| 5,741,271 A | 4/1998 | Nakao et al. | |
| 5,766,134 A | * 6/1998 | Lisak et al. | 600/562 |
| 6,322,522 B1 | * 11/2001 | Zimmon | 600/565 |
| 6,506,166 B1 | * 1/2003 | Hendler et al. | 600/562 |
| 2002/0038125 A1 | * 3/2002 | Hamilton | 606/115 |

FOREIGN PATENT DOCUMENTS

WO    WO 00/12011    3/2000

\* cited by examiner

Primary Examiner—Max F. Hindenburg
Assistant Examiner—Jonathan Foreman
(74) Attorney, Agent, or Firm—Knobbe, Martens, Olson & Bear, LLP

(57) ABSTRACT

A system and method provides for the capture of body tissue samples such as lymph nodes. The system includes a bag formed of a flexible material having a first end opened for receiving the body tissue sample and a second end which is closed to the body tissue sample but which permits a vacuum to be pulled through the bag. The system further includes a vacuum tube in which the body tissue sample capture bag may be disposed and a vacuum source that pulls a vacuum through the body tissue sample capture bag for pulling the body tissue sample into the bag through the opened end of the bag.

18 Claims, 2 Drawing Sheets

SYSTEM AND METHOD FOR CAPTURING BODY TISSUE SAMPLES

BACKGROUND OF THE INVENTION

The present invention is generally directed to a system and method for capturing body tissue samples. The present invention is more particularly directed to such a system and method which finds particular application for the isolation, resection, and capture of lymph nodes or other tissue.

One important step in the treatment of pulmonary cancer is nodule resection for staging. Staging refers to the evaluation of organ compromise and cancer dissemination when a nodule is discovered and cancer is suspected. One important surgical step of staging is the sampling of bronchial lymph nodes.

One frequently employed procedure to sample lymph nodes in the thorax and bronchial system is mediastinoscopy. Through an incision made on the anterior portion of the neck, a tubular instrument called a mediastinoscope is inserted and placed anterior to the trachea. The mediastinoscope permits direct visualization of the lymph nodes located in the paratracheal and parabronchial areas. The size of the instrument is large enough to allow the insertion of grabbing tools to dissect regional lymph nodes during surgery. Once removed, the resected lymph nodes are sent to pathology for analysis. This procedure is routinely done before thoracic surgery is performed in most patients with thoracic tumors, in particular, suspected lung cancer.

Although bronchial lymph node visualization and resection through the mediastinoscope is commonly performed, the procedure is not without its problems. For example, the procedure is limited to the taking of one lymph node sample at a time. Since a plurality of lymph node samples are generally required to be resected for proper staging, the procedure can be relatively long. In addition, the instrumentation to grab and resection the lymph node samples is often the cause of problems. For example, surgeons generally utilize long instruments like ring forceps to suspend the target lymph node to be resected and removed. Such instruments can result in the potential squeezing and damage to lymph nodes that may contain cancer cells. Obviously, this is a condition to be avoided.

Hence, there is a need in the art for an improved system and method for the capturing of body tissue samples. More particularly, there is such a need for a system and method for capturing bronchial and thoracic lymph nodes suspected of being cancerous. The present invention addresses that need.

SUMMARY OF THE INVENTION

The present invention provides a system for capturing a body tissue sample including a bag formed of a flexible material which includes a first end being opened for receiving a body tissue sample and a second end closed to the body tissue sample and a vacuum tube that receives the bag and directs a vacuum pull through the bag for pulling the body tissue sample into the bag through the first end of the bag.

The bag is preferably elongated from the first end to the second end. Further, the second end of the bag may be configured to permit the body tissue sample to be confined in the bag while permitting the vacuum to pull the body tissue sample into the bag through the first end of the bag. To that end, the bag may include a plurality of holes or be formed from a mesh material.

The vacuum tube may be configured for receiving the bag therein and having a first end for making sealing engagement with the bag first end and having a second end configured for coupling to a vacuum source.

The vacuum tube may include a vacuum control that selectively applies and regulates the vacuum pull to the bag. The vacuum control may be an orifice in the vacuum tube.

The vacuum tube has an inner diameter and preferably a stop mechanism that selectively reduces the inner diameter of the vacuum tube. The stop mechanism may be adjacent the first end of the vacuum tube to initially capture the body tissue sample in the bag between the first end of the vacuum tube and the stop mechanism when the inner diameter of the vacuum tube is reduced. The stop mechanism is further preferably returnable to the inner diameter of the vacuum tube to permit the body tissue sample to be pulled to the second end of the bag.

The present invention still further provides a system for capturing a body tissue sample which includes bag means formed of a flexible material and including an opened end for receiving a body tissue sample and a closed end for capturing the body tissue sample. The system further includes a vacuum tube means for receiving the bag means and directing a vacuum pull through the bag means to pull the body tissue sample into the bag means through the opened end of the bag means.

The present invention still further provides a method of capturing a body tissue sample including the steps of disposing a body tissue sample capture bag adjacent to the body tissue to be sampled, drawing a vacuum through the body tissue sample capture bag to suspend the body tissue sample to be sampled, resecting the body tissue sample, and drawing the body tissue sample into the body tissue sample capture bag under the influence of the vacuum drawn through the body tissue sample capture bag.

The method further includes the steps of loading the body tissue sample bag into a vacuum tube, coupling the vacuum tube to a vacuum source, and energizing the vacuum source to draw the vacuum through the body tissue sample capture bag. The method preferably further includes the steps of reducing a dimension of the vacuum tube before resectioning the body tissue sample to capture the body tissue sample in a proximal portion of the body tissue sample capture bag. Thereafter, the original dimension of the vacuum tube may be restored to draw the body tissue sample to a distal portion of the body tissue sample capture bag under the influence of the vacuum drawn through the body tissue sample capture bag.

BRIEF DESCRIPTION OF THE DRAWINGS

The features of the present invention which are believed to be novel are set forth with particularity in the appended claims. The invention, together with further advantages thereof, may best be understood by making reference to the following description taken in conjunction with the accompanying drawings, in the several figures of which like reference numerals identify identical elements, and wherein:

DETAILED DESCRIPTION OF THE PREFERRED EMBODIMENTS

Figure 1:
FIG. 1 is a side view of a body tissue sample capture bag embodying the present invention.

Referring now to FIG. 1, it illustrates a body tissue capture bag 10 embodying the present invention. The bag 10 is preferably formed of a flexible material and may be formed from silicon rubber, polyurethane, expanded polytetraflourouthylene, polyester, or a combination of these materials, for example. The bag 10 includes a first end 12 and a second end 14. The first end 12 is open for receiving a body tissue sample therein. The second end 14 is closed to the body tissue sample to be captured. The second end 14 more particularly is configured to permit the body tissue sample to be captured while enabling a vacuum to be pulled through the bag from the first end 12 to the second end 14. In accordance with this embodiment, the second end 14 therefore includes a plurality of holes 16, each being smaller in dimension than the tissue sample. Alternatively, the second end 14 of the bag 10 may be formed from a mesh material.

Figure 2:
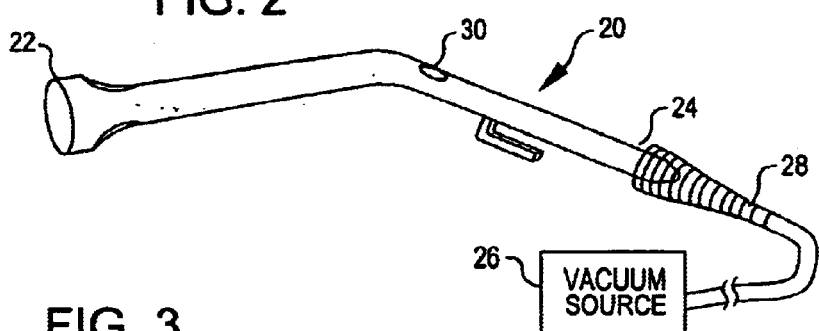
FIG. 2 is a side view of a vacuum tube and vacuum source which may be utilized in conjunction with the body tissue sample capture bag of FIG. 1 to comprise a system for capturing a body tissue sample embodying the present invention.

FIG. 2 shows a vacuum tube 20 for use with the body tissue sample capture bag 10 of FIG. 1. The vacuum tube includes a first end 22 and a second end 24. The first end 22 is dimensioned to receive the body tissue sample capture bag therein as will be seen subsequently in FIG. 4. The second end 24 of the vacuum tube 20 is configured for being coupled to a vacuum source 26 by a coupling 28.

The vacuum tube include an orifice 30 which forms a vacuum control. When the orifice 30 is uncovered as illustrated, a vacuum is pulled by the vacuum source 26 through the orifice 30 and the coupling 28. However, when the orifice 30 is covered, the vacuum is then pulled through the vacuum tube from the first end 22 to the second end 24 and through the coupling 28. Hence, when the body tissue sample capture bag 10 is disposed within the vacuum tube 20 and the orifice 30 is covered, the vacuum pull will be directed through the body tissue sample capture bag 10 from its first end 12 to its second end 14 by the vacuum tube 20.

Figure 3:
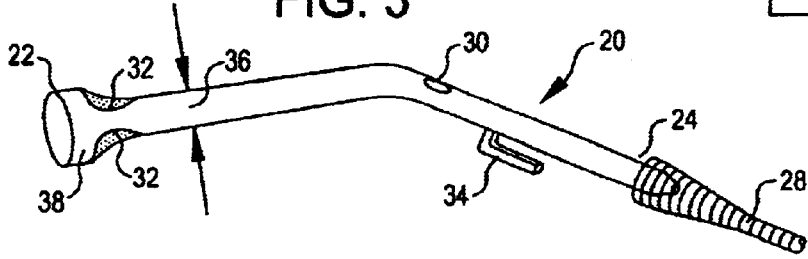
FIG. 3 is a side view of the vacuum tube of FIG. 2 illustrating additional functions thereof.

As may be best seen in FIG. 3, the vacuum tube 20 further includes a stop mechanism which may be activated by the depression of a trigger 34. To this end, it will be noted that the vacuum tube 20 has an inner diameter dimension 36 which is reduced by the stop mechanism 32 when the trigger 34 is depressed. This forms or creates a proximal cavity, compartment, or portion 38 in the vacuum tube 20 between the first end of the vacuum tube 20 and the stop mechanism 32 for the initial capture of the body tissue sample as will be seen hereinafter.

Figure 4:
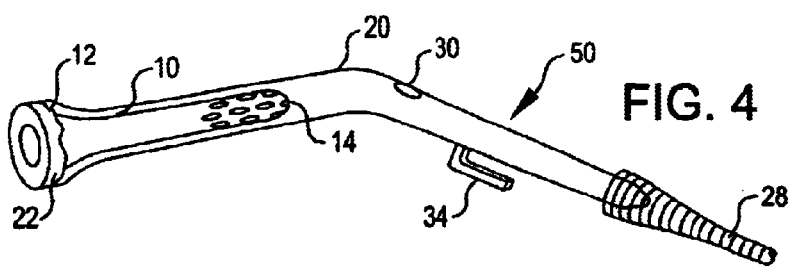
FIG. 4 is a side plan view of the body tissue sample capture system embodying the present invention.

FIG. 4 shows the body tissue sample capture system 50 which is fully assembled and ready for use. Here it may be seen that the body tissue sample capture bag 10 has been disposed within the vacuum tube 20 with the first end 12 of the body tissue sample capture bag being in sealing engagement with the first end 22 of the vacuum tube 20. As will also be noted in FIG. 4, the orifice 30 is distal to the distal or second end 14 of the body sample capture bag 10. Hence, even though the vacuum source may be activated, the vacuum is pulled from the orifice 30 through the coupling 28 and not through the body sample capture bag 10 at this time.

Figure 5:
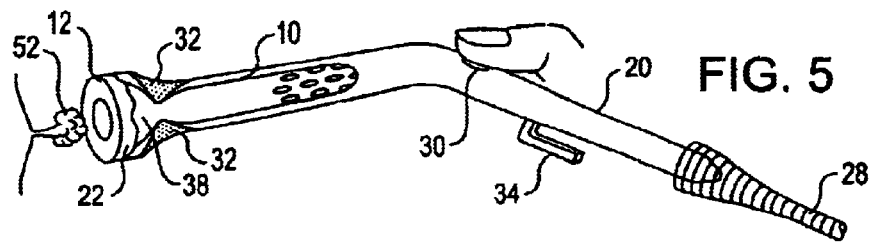
FIG. 5 is a side plan view of the system of FIG. 4 illustrating a first step in capturing a body tissue sample.

As seen in FIG. 5, when the orifice 30 is covered by a finger of the physician, the vacuum is now pulled through the body tissue sample capture bag 10. When the first end 22 of the vacuum tube 20 is disposed adjacent to the body tissue to be sampled, such as a lymph node 52, the lymph node 52 will be suspended at the first end 22 of the vacuum tube 20 and hence the first end 12 of the body tissue sample capture bag 10. As will be also noted in FIG. 5, the trigger 34 has been depressed to cause the stop mechanism to reduce the inner diameter of the vacuum tube 20 to create the proximal portion or space 38.

Figure 6:
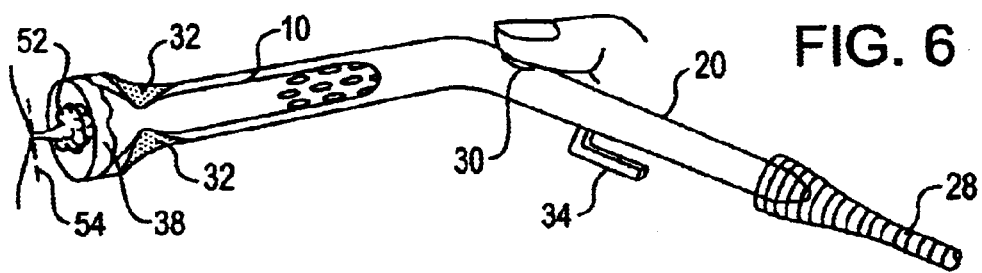
FIG. 6 is a side view of the body tissue sample capture system in use during an intermediate step of capturing a body tissue sample in accordance with the present invention.

As shown in FIG. 6, the lymph node 52 is now resectioned at a section line 54 and captured in the proximal space or compartment 38 formed by the stop mechanism 32. The lymph node 52 is held within the bag 10 within the space 38 by the stop mechanism 32 and the vacuum pull created by the vacuum source which is pulled through the body tissue sample capture bag 10, the vacuum tube 20, and the coupling 28.

Figure 7:
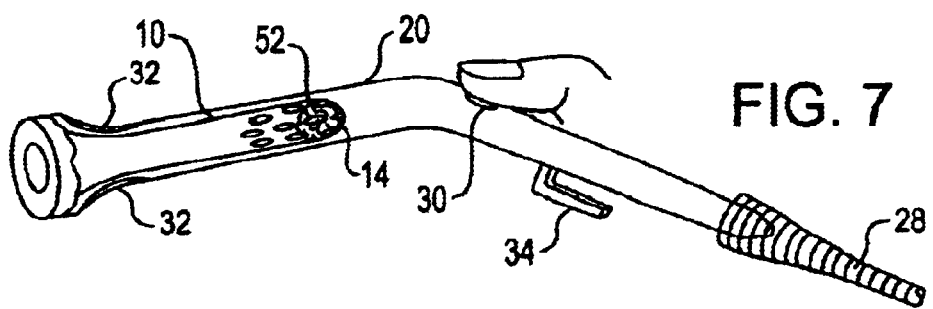
FIG. 7 is another side view of the body tissue sample capture system during a final stage of the body tissue sample capturing method embodying the present invention.

Lastly, as is best seen in FIG. 7, the trigger 34 is released to cause the stop mechanism 32 to return the inner diameter of the vacuum tube 20 to its original inner diameter. This causes the lymph node 52 to be drawn under the influence of the pulled vacuum further into the body tissue sample capture bag 10 and, more specifically, to the second end 14 of the body tissue sample capture bag 10. Now that the lymph node 52 has been captured, a further lymph node can be captured as illustrated in FIGS. 5–7 and as described above. When all of the lymph nodes have been captured, the orifice 30 may be uncovered to release the vacuum pull from the body tissue sample capture bag 10, whereupon, the body tissue sample capture bag 10 may be removed from the vacuum tube 20 and the lymph nodes captured therein labeled and sent to pathology for analysis.

As can thus be seen, the present invention provides a new and improved system for capturing one or more body tissue samples. More particularly, the system and method of the present invention is more gentle on the body tissue samples to be collected since the physical grabbing of the body tissue is not necessary. Further, more than one body tissue sample may be captured during a single procedure thus shortening the surgical procedure.

While a particular embodiment of the present invention have been shown and described, modifications may be made. For example, the system and method of the present invention may be used for collecting and capturing body tissue samples other than lymph nodes. It is therefore intended to cover in the appended claims all such changes and modifications which may fall within the true spirit and scope of the invention as defined by the appended claims.

What is claimed is:

1. A system for capturing a body tissue sample comprising:
   a bag formed of a flexible material, the bag including a first end and a second end, the first end being opened for receiving a body tissue sample and the second end being closed to the body tissue sample;
   a vacuum tube that receives the bag and directs a vacuum through the bag for pulling the body tissue sample into the bag through the first end of the bag, the vacuum tube having a first end and a second end, the vacuum tube being configured to receive the bag therein with the bag first end in sealing engagement with the vacuum tube first end and the vacuum tube second end being configured for coupling to a vacuum source, the second end of the bag being configured to permit the body tissue sample to be confined in the bag while permitting the vacuum to pull the body tissue sample into the bag through the first end of the bag; and an inner diameter defined within the vacuum tube and a stop mechanism that selectively reduces the inner diameter.

2. The system of claim 1, wherein the bag is elongated from the first end to the second end.

3. The system of claim 1, wherein the second end of the bag includes at least one hole, the at least one hole being smaller in dimension than the body tissue sample.

4. The system of claim 1, wherein the vacuum tube includes a vacuum control that selectively applies the vacuum pull to the bag.

5. The system of claim 4, wherein the vacuum control includes an orifice in the vacuum tube.

6. The system of claim 1, wherein the stop mechanism is adjacent the first end of the vacuum tube, to initially capture the body tissue sample in the bag between the first end of the vacuum tube and the stop mechanism when reducing the inner diameter.

7. The system of claim 6, wherein the stop mechanism is returnable to the inner diameter of the vacuum tube to permit the body tissue sample to be pulled to the second end of the bag.

8. A system for capturing a body tissue sample comprising:

bag means formed of a flexible material and including an opened end for receiving a body tissue sample and a closed end for capturing the body tissue sample, the closed end including means for capturing the body tissue sample while permitting a vacuum to be pulled from the opened end of the bag through the closed end of the bag;

a vacuum tube means for receiving the bag means and directing a vacuum pull through the bag means to pull the body tissue sample into the bag means through the opened end of the bag means, the vacuum tube means having a first end and a second end, the vacuum tube means for receiving the bag therein with the bag opened end in sealing engagement with the vacuum tube means first end and the vacuum tube means second end being configured for coupling to a vacuum source; and wherein the vacuum tube means has an inner diameter and a stop means for selectively reducing the inner diameter.

9. The system of claim 8, wherein the bag means is elongated from the opened end to the closed end.

10. The system of claim 8, wherein the closed end of the bag includes at least one hole, the least one hole being smaller in dimension than the body tissue sample.

11. The system of claim 8, wherein the vacuum tube means includes control means for selectively applying the vacuum pull to the bag means.

12. The system of claim 11, wherein the vacuum control means includes an orifice in the vacuum tube.

13. The system of claim 8, wherein the stop means is adjacent the first end of the vacuum tube for initially capturing the body tissue sample in the bag means between the first end of the vacuum tube and the stop means when reducing the inner diameter.

14. The system of claim 13, wherein the stop means is returnable to the inner diameter of the vacuum tube means for permitting the body tissue sample to be pulled to the closed end of the bag.

15. A method of capturing a body tissue sample, the method including the steps of:

loading a body tissue sample capture bag into a vacuum tube;

coupling the vacuum tube to a vacuum source;

disposing a body tissue sample capture bag adjacent to the body tissue to be sampled;

drawing a vacuum through the body tissue sample capture bag to suspend the body tissue to be sampled;

resectioning the body tissue sample; and drawing the body tissue sample into the body tissue sample capture bag under the influence of the vacuum drawn through the body tissue sample capture bag.

16. The method of claim 15, including the further step of reducing a dimension of the vacuum tube before resectioning the body tissue sample to capture the body tissue sample in a proximal portion of the body tissue sample capture bag.

17. The method of claim 16 including the further step of restoring the dimension of the vacuum tube after capturing the body tissue sample in the proximal portion of the body tissue sample capture bag to draw the body tissue sample to a distal portion of the body tissue sample capture bag under the influence of the vacuum drawn through the body tissue sample capture bag.

18. A method of capturing a body tissue sample, the method comprising the steps of:

disposing a body tissue sample capture bag adjacent to the body tissue to be sampled;

reducing a radial dimension of the body tissue sample bag;

drawing a vacuum through the body tissue sample capture bag to suspend the body tissue to be sampled;

resectioning the body tissue sample; and drawing the body tissue sample into the body tissue sample capture bag under the influence of the vacuum drawn through the body tissue sample capture bag by expanding the radial dimension of the body tissue sample bag.

* * * * *